(12) United States Patent
Anderson et al.

(10) Patent No.: US 6,325,776 B1
(45) Date of Patent: Dec. 4, 2001

(54) INTERNAL BY-PASS SHUNT APPARATUS FOR THE INFERIOR VENA CAVA

(76) Inventors: Bernard Bradley Anderson, 3400 Pennsylvania Ave., SE., Washington, DC (US) 20020; Abraham Antonio Anderson, 1910 $9^{th}$ St., #4, Berkeley, CA (US) 94710

( * ) Notice: Subject to any disclaimer, the term of this patent is extended or adjusted under 35 U.S.C. 154(b) by 0 days.

(21) Appl. No.: 09/371,045

(22) Filed: Aug. 10, 1999

Related U.S. Application Data (62) Division of application No. 09/023,488, filed on Feb. 13, 1998, now Pat. No. 6,148,825.

(51) Int. Cl.$^7$ .................................................. A61F 13/20
(52) U.S. Cl. ......................................... 604/8; 604/101.01
(58) Field of Search ................................... 604/8, 101.01, 604/96.01

(56) References Cited

U.S. PATENT DOCUMENTS

| | | | |
|---|---|---|---|
| 4,950,266 | * | 8/1990 | Barron ....................................... 604/8 |
| 5,879,321 | * | 3/1999 | Hill ........................................... 604/8 |
| 5,893,841 | * | 4/1999 | Glickman .............................. 604/101 |
| 5,928,181 | * | 7/1999 | Coleman et al. ........................ 604/8 |

* cited by examiner

Primary Examiner—Dinh X. Nguyen
(74) Attorney, Agent, or Firm—Lalos & Keegan (57) ABSTRACT

The apparatus for diverting blood from the retro hepatic inferior vena cava (IVC) and internally shunting renal and infra renal IVC blood into the right atrium during surgery on the liver, its vessels, or the retro hepatic IVC is described. It is symmetrical on its mid horizontal axis permitting similar utility whether venous access was above or below the liver. It is a hollow plastic tube with two sidewall openings, one at each end with four intervening completely encircling balloons. It is continuous with a proximal component which serves to remotely manipulate, infuse fluids and inflate the balloons in the distal component. Once introduced into the venous system by right atriotomy or infrarenally by venotomy, the distal component would be advanced and seated in the right atrium and supra renal IVC. Inflation of the balloon immediately below the shunt opening in the right atrium would provide for easy digital sensation within the pericardium and identification of the exact site below this balloon for occlusion by ligating the intra pericardial IVC around the shunt. This would prevent reflux of blood from the heart into the retro hepatic IVC and fix the position of the balloon immediately above the lower opening cephalad to the renal veins which when inflated would occlude the supra renal IVC and instantly cause bypass of the retrohepatic IVC, and shunt renal and infra renal IVC blood to the heart.

22 Claims, 5 Drawing Sheets

INTERNAL BY-PASS SHUNT APPARATUS FOR THE INFERIOR VENA CAVA

CROSS-REFERENCE TO RELATED APPLICATIONS

This application is a Divisional of Application Ser. No. 09/023,488 filed Feb. 13, 1998, for A Method of Using A Dedicated Internal Shunt and Stent for Inferior Vena Cava now U.S. Pat. No. 6,148,825.

BACKGROUND

The Inferior Vena Cava (IVC) is the largest vein in the body returning the majority of the venous return to the heart. The mean diameter has been reported to be 20 m.m. with a range from 13 to 30 m.m. with a standard deviation of 3 m.m.—see Prince, M R et al. in Radiology 1983, December: 149 (3) 687–9.

The (1) Retrohepatic vena cava, (2) Vena cava between the Right atrium and the Right renal vein, (3) The Supra hepatic vena cava, have been measured by Rodrigues A. J. Junior et al., Gegerbaurs Morphol. Jahrb 1987, 133 (4); 665–72. and reported respectively to be: (1) 78.34 m.m., (2) 135. 16 m.m. and (3) 19.34 m.m.

Additionally, Dr. Hee Lee at the District of Columbia General Hospital (Table I) has measured the IVC in adult men and women utilizing the Computerized Tomogram and found the average length of the vena cava from the right atrium to the left renal vein to be 134.2 m.m. and 124.4 m.m. in males and females respectively; and 132.2 m.m. and 123.6 m.m. in males and females respectively from the right atrium and the right renal vein.

The IVC is often injured in penetrating trauma to the abdomen. Mortality is especially high-in the order of 90% when the retro hepatic vena cava is involved primarily for the following reasons:

1. Massive hemorrhage often results from disruption of the vena cava or attempts to expose the injured vessel in this difficult to access area lying posterior to the liver.

2. Acute interruption of the IVC by clamping the IVC above and below the liver may produce a nonperfused retrohepatic segment but severely reduces the venous return to the heart with the consequence of inadequate cardiac output and venous congestion and metabolic disturbances in the abdominal viscera and the lower extremities that often result in the death of the patient.

In an attempt to avert the disastrous consequences of hemorrhage and the acute interruption of venous return consequent to IVC interruption described above, surgeons have historically created an internal vena cava shunt mainly by one of two techniques: In the first technique, a chest tube has been placed into the IVC through the right heart after which the IVC would be encircled above and below the liver and tied down to the internal chest tube thereby creating an avascular segment in the area of injury and an internal shunt allowing blood to return to the heart through an opening in the chest tube customized to lie within the right atrium. This technique is often unsuccessful as encircling the vena cava below the liver can be difficult and can also result in inadvertent injury to other vessels with consequent bleeding from additional sites.

In a second technique, surgeons have employed an endotracheal tube to insert into the IVC similarly through the right atrium, followed by ligation of the intrapericardial IVC around the endotracheal tube after which the balloon of the endotracheal tube would be blown up in the suprarenal IVC forcing the blood to shunt into the lower opening of the tube and exit through an opening customized to lie in the atrial portion of the tube. In this manner the circlage of the vena cava below the liver with its inherent potential problems would be avoided.

In the two techniques above, one has to make a judgment each time how far to insert the tube, where to customize the atrial opening and where to place the inferior ligature or inflate the balloon with respect to the renal veins and where to apply the proximal ligature with respect to the proximal customized opening in the tube to permit venous return to the heart.

Given the above anatomic, physiologic and technical considerations, an improved shunt for the retrohepatic IVC is hereby proposed that would:

1.) Be based on the known anatomic dimensions of the adult suprarenal IVC.

2.) Eliminate the need for customization of devices not originally intended for the shunting of blood or for use in this location.

3.) Provide a method for the easy and accurate identification of the site within the pericardium for the fixation of the device within the venous system which would also occlude the IVC above the retrohepatic IVC thereby preventing reflux of blood from the heart; and also obligate the caudal IVC occlusion balloon to position below the retrohepatic IVC segment; which when inflated would provide for bypass of the retrohepatic IVC and an internal shunt of blood from the renal veins and the suprarenal IVC to return to the heart.

This dedicated IVC shunt and stent, hereafter referred to as the Anderson Shunt, is depicted in FIGS. 1, 2, 3, 4, 5, 1C and 2C, and is described in the following specifications and descriptions:

BRIEF DESCRIPTION OF THE DRAWINGS

(2) The intrapericardial ligation of the suprahepatic IVC around the shunt at the atriocaval junction preventing reflux of blood from the heart into the retrohepatic IVC also achieving fixation of the device within the venous system.

(3) Suprarenal occlusion of the IVC around the shunt above the caudal opening.

(4) The isolated retrohepatic vena cava optimized for surgery.

(5) The inflated intraatrial balloon which defines the exact site for ligation and device fixation described in (2) and (6) The orifice in the shunt above the atrial balloon which provides for venous return from the shunt to the heart.

DETAILED DESCRIPTION OF THE INVENTION

The invention is depicted in FIGS. 1, 1C, 2, 2C, 3, 4 and 5 in the appended drawings.

Figure 1:
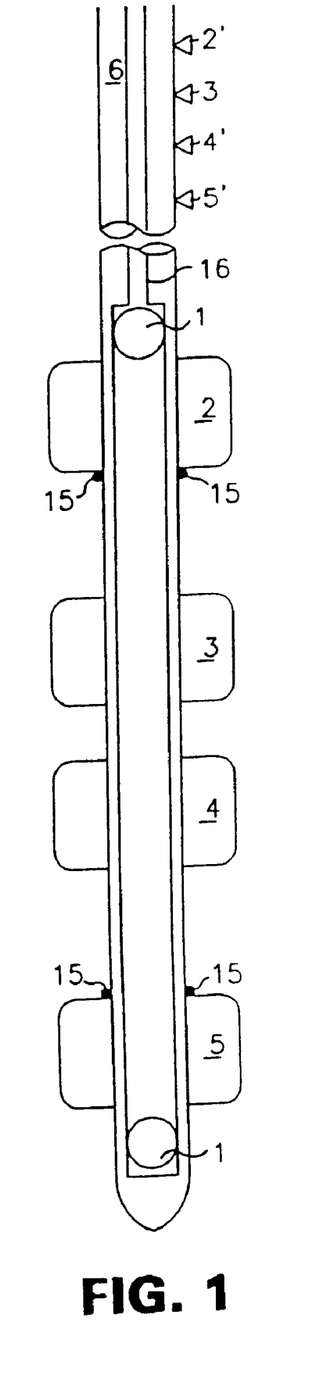
FIG. 1 is a full longitudinal cross sectional view of the shunt for insertion into the vena cava through a right atriotomy showing the balloons in an inflated posture. These balloons when deflated would collapse around the shunt.

FIG. 1 is a longitudinal cross sectional detail of the device on a 1:1 scale.

Figure 1C:
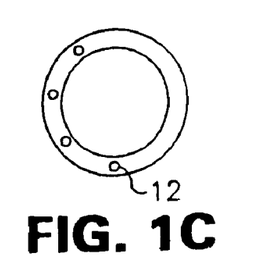

FIG. 1C is a horizontal cross sectional detail of the device in its distal portion, on a 2:1 scale.

The entire device is a flexible plastic tube approximating 50 centimeters (cm) long and 13 millimeters (m.m.) wide. The internal diameter of the tube is 10 m.m. with a wall thickness of 3 m.m.

The device consists of a distal portion of critical dimensions and is designed for complete embodiment within the adult right atrium and suprarenal IVC and is 160 m.m. long.

There are two 10 m.m. diameter orifices in the device on either end of this distal portion to allow for blood to enter the shunt from the IVC, traverse the shunt and exit the shunt in the right atrium. These orifices are labeled 1 and there is an exact distance of 140 mm, mid-orifice to mid-orifice.

Four inflatable balloons encircle this distal portion of the shunt between these two orifices and are labeled 2, 3, 4, and 5. Each balloon would occupy a 20 m.m. length of the tube and would be able to be inflated up to a 35 m.m. diameter and be sufficient to occlude the IVC with a known mean diameter of 20 m.m. Balloons 2 and 5 are essential to the operations of the shunt. Inflation or deflation of the intervening balloons lend flexibility to the shunt and may or may not be used in its operation depending on the nature of injury to the retrohepatic vena cava.

Balloon labeled 2, when sufficiently inflated within the right atrium provides for digital sensation within the pericardium of the appropriate point for fixation of the device within the venous system by ligation of the intrapericardial IVC around the shunt in the venous system immediately caudal to balloon 2. This critical point is also marked by a 1 mm circular ridge on the outside of a tube 15 which may provide for an alternate or added site for tactile sensation. When so introduced, sensed and fixed, the cephalad 30 m.m. of this distal portion of the tube would lie within the right atrium with the remaining 130 m.m. of the distal portion of the device positioned in the suprarenal IVC cephalad to the renal vein orifices.

Balloon #5 occupies a 20 m.m. segment of the tube between 20 to 40 m.m. from the caudal tip of the distal segment. It sits immediately cephalad to the caudal orifice of the shunt and when inflated sufficiently, it serves to occlude the suprarenal IVC safely cephalad to the renal veins orifices by a distance of approximately 25 m.m. The length of tube between balloons 2 and 5 is 90 m.m. and would approximate the difficult to access retrohepatic IVC. Following intrapericardial ligation of the IVC around the shunt and suprarenal occlusion of the IVC as described above, the desired bypass of the retrohepatic IVC and the return of blood from the renal veins and infrarenal IVC to the heart would have been simply and expeditiously achieved.

The proximal portion of the device is continuous with the distal portion detailed above and is intended for only partial embodiment within the venous system. It serves to carry 4 tubular conduits of variable lengths in the wall of the device labeled 12 that connect balloons labeled 2–5 with respective inflation ports labeled 2'–5' located in the most proximal 5 cm. of the device labeled 6 such that port 2' would connect to balloon 2, port 3' to balloon 3 and so on. This proximal portion also provides a means to manipulate the distal portion of the device within the venous system as well as providing for the introduction of fluids to the distal portion by way of a 2 mm central tube 16, connecting to a venous access port 17, at the most proximal end of the device.

The ports would be Laur lock in design and the inflation fluid would be normal saline. The device described in FIG. 1 and 1C is designed for introduction into the venous system by way of a right atriotomy.

Figure 2:
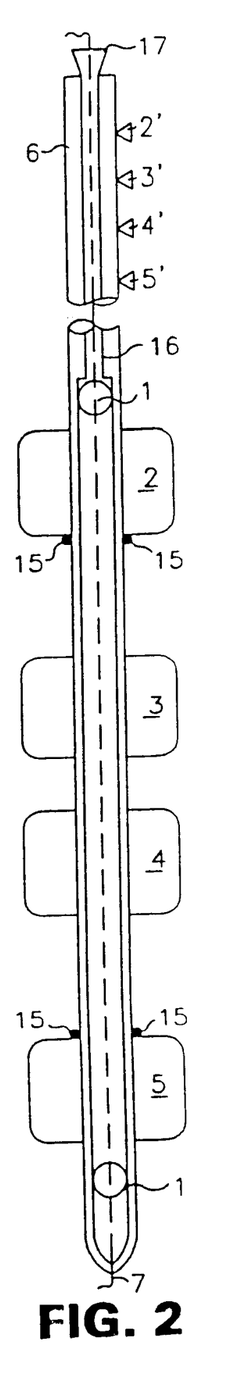
FIG. 2 depicts a narrower variation of the shunt of FIG. 1 modified in design to include a guide wire for optional Seldinger type access of the venous system either above or below the liver.

FIG. 2 is essentially the same device in FIG. 1 having the same longitudinal dimensions and all the elements and details of FIG. 1 with the following differences.

1.) The tube has a smaller diameter. Its external diameter would be 10 m.m. while its internal diameter would be 7 m.m.

2.) The orifices labeled 1 in FIG. 2 would have a 7 m.m. diameter, the same as the diameter of this smaller tube.

3.) There would be an additional tubular conduit traversing the length of the device for accommodating a flexible guide wire over which the tube could be passed according to the Seldinger technique.

Figure 2C:
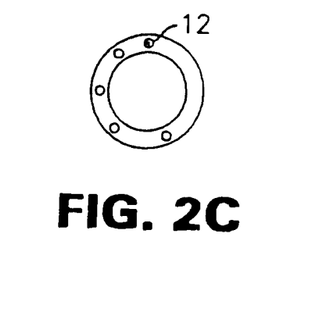

FIG. 2C is a 2:1 horizontal cross sectional detail of the device in FIG. 2 taken in the critical distal portion showing its narrower diameter and an additional conduit in the wall of the tube for the accommodation of a guide wire.

The device described in FIG. 2 and FIG. 2C is designed for introduction into the venous system by way of a right atriotomy as is the device depicted in FIG. 1, but because of its smaller size, it may be suitable for introduction into the venous system above or below the liver by way of a right internal jugular vein cutdown or a right iliac vein or a right long saphenous vein cutdown.

Figure 3:
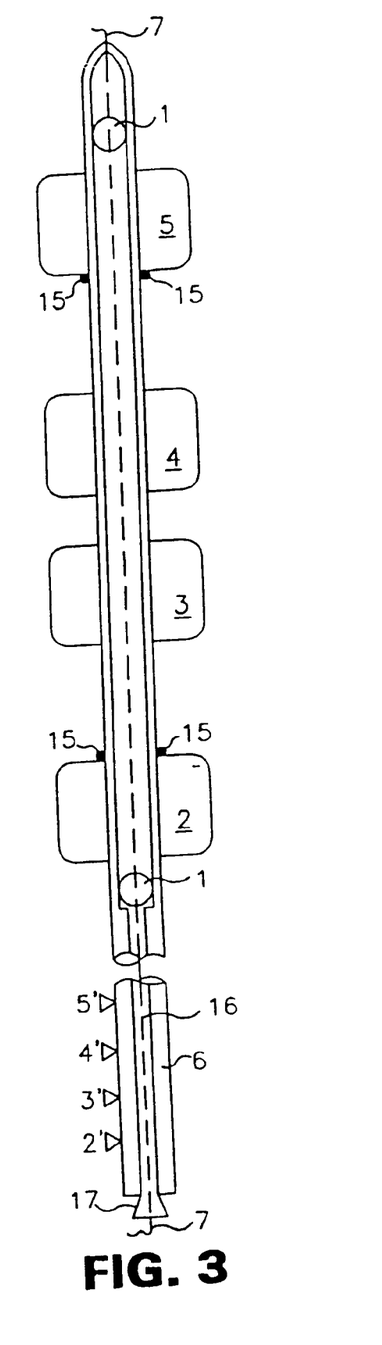
FIG. 3 depicts the shunt in FIG. 2 in an attitude of infrahepatic insertion.
Figure 4:
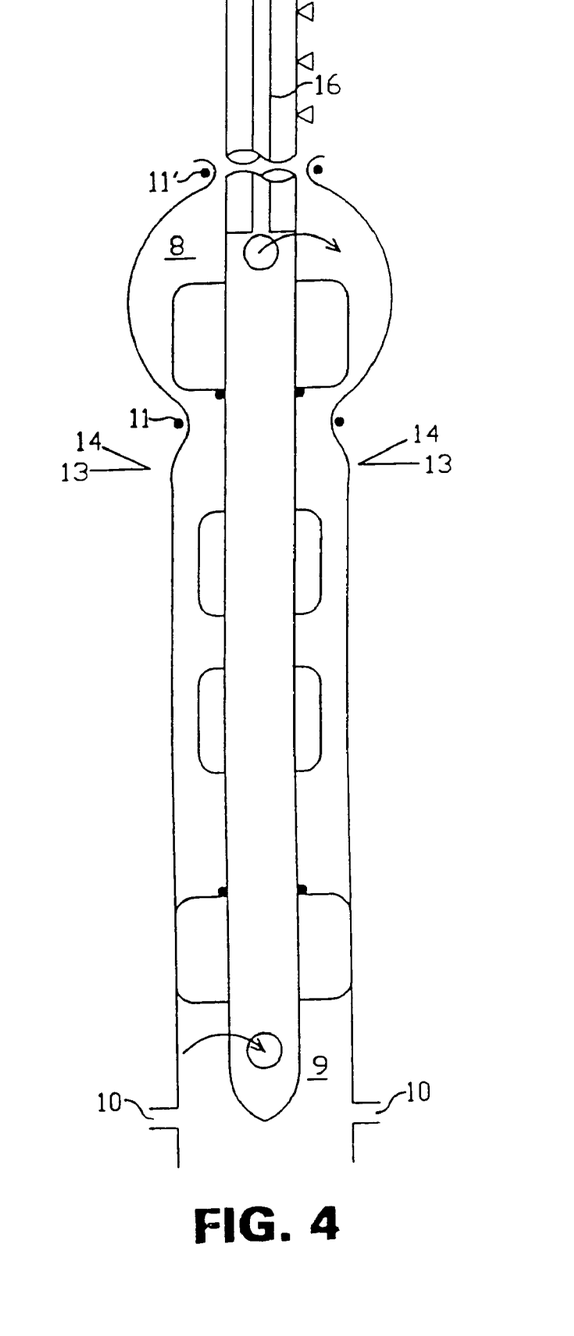
FIG. 4 is a figurative drawing of the device functionally seated in the venous system showing (1) The shunting of blood from the renal veins and infrarenal IVC entering the caudal opening of the shunt.

FIG. 3 is the same device in FIG. 2 in an attitude of infrahepatic insertion. FIG. 4 is a graphical depiction of the device functionally seated in the venous system with the complete embodiment of the distal segment of the device within the right atrium labeled 8, and the suprarenal IVC labeled 9, showing closure of the right atriotomy site with a prolene suture -11' around the proximal portion of the device; closure of the intrapericardial IVC around the shunt below the atrial balloon with umbilical tape-11; and, an inflated suprarenal IVC occlusion balloon. Two arrows depict the entrance of blood into the orifice above the renal veins and the exit of blood into the right atrium. The two intervening balloons are shown partially inflated. Note the renal veins -10, the diaphragm -13 and the pericardium -14.

Figure 5:
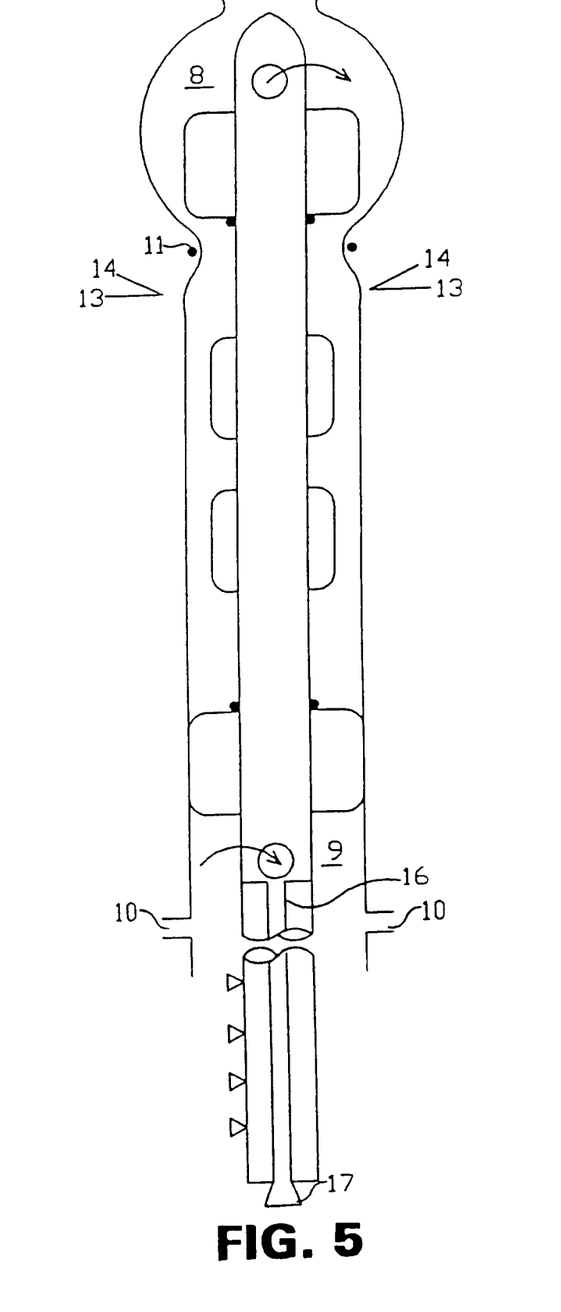
FIG. 5 is a figurative drawing of the device functionally seated in the venous system and showing venous access below the renal veins.

As depicted in FIGS. 4 and 5 the retrohepatic IVC would be isolated, bypassed and in an optimal condition for surgery. A Legend for the dedicated IVC shunt (Anderson Shunt) is described in Table II.

Indications for Use

The use of the shunt is projected to facilitate the control of hemorrhage in the following instances:

1.) When the hepatic veins or the retrohepatic IVC is suspected to have been injured.

2.) When significant bleeding is anticipated or realized during elective or emergent resection of the liver for tumors or for trauma.

Technique for Supradiaphragmatic Insertion of the Device

The device depicted in FIG. 1 and its "percutaneous" modification which is smaller and depicted in FIG. 2 are preferably inserted in the venous system via a right atriotomy.

The smaller device may additionally be inserted into the venous system by way of an internal jugular vein cutdown. With the exception of the site of access the technique of insertion is the same as when the venous access site was the right atrium. The preferred right atriotomy access and insertion of the device is detailed below.

(1) The abdominal midline incision used for exploratory laparotomy would be extended upwards into the sternum.

(2) The pericardium would be opened and the intrapericardial IVC would be encircled with umbilical tape.

(3) The right atrial appendage would be used to access the IVC through an atriotomy encircled by a purse string suture of prolene.

(4) The device filled with normal saline would be inserted through the atriotomy and advanced through the atrium into the IVC to a distance just beyond the atrial shunt opening—numbered -1- in the appended drawing. The atrial balloon labeled -2- would be inflated with just enough saline, injected through port 2', to be sensed by the fingers on the intrapericardial IVC within the open pericardium. Determination of the optimum position for ligation of the intrapericardial IVC is facilitated by the presence of a circular ridge on the external wall of the shunt to detect the site for placement of the ligation.

(5) At this point there would be no further advance of the device, and the previously placed umbilical tape - 11, in FIG. 4 would be tightened to collapse the intrapericardial vena cava around the device thereby preventing blood from passing into the retrohepatic vena cava from the right atrium and also fixing the correct length of the shunt in the suprarenal IVC. This location was notable to be detected by the presence of the circular ridge below the atrial balloon.

(6) At this time inflation of the lowermost balloon -5 would be done by injection of saline through port 5' thereby achieving occlusion of the suprarenal IVC.

Following completion of steps 1–6, the retrohepatic IVC would be isolated and blood from the kidneys and the infrarenal IVC would enter the shunt seated above the renal veins, bypass the retrohepatic IVC and return to the heart by way of the atrial orifice of the device.

N.B. The intervening balloons 3 and 4 could be inflated optionally through ports 3' and 4' yielding further flexibility if such was desired depending on the nature of the injury.

Technique for Infradiaphragmatic Insertion of the Device

There may be occasions—anatomic or technical when introduction of the shunt via a venous access point below the diaphragm and liver is preferred. In such instances the smaller modification of the shunt may be applicable for insertion via a right external iliac vein cutdown, or via a right long saphenous vein cutdown.

The attitude of the tube in such insertion is depicted in FIG. 3 in which case the technique of insertion would be as follows:

(1) The midline abdominal incision used for exploratory laparotomy would be extended upwards into the sternum.

(2) The pericardium would be opened and the intrapericardial IVC would be encircled with umbilical tape.

(3) The right iliac vein or right long saphenous vein would be isolated and controlled proximal and distal to the intended venotomy site.

(4) The venotomy would be effected and the saline filled device would be inserted into the venous system with or without use of the guide wire and the Seldinger technique.

(5) The device would then be advanced into the IVC and right atrium where the atrial balloon—now balloon 5—would be inflated and retracted enough that the balloon could be sensed digitally by fingers on the intraperdicardial IVC, if the circular ridge at the base of the balloon wall of the shunt was not alternately detected.

(6) At this point approximating the atrio-caval junction, the previously placed umbilical tape encircling the intrapericardial IVC would be tightened around the shunt immediately caudal to the atrial balloon of the device within the venous system thereby preventing blood from refluxing into the retrohepatic IVC from the right atrium, as well as fixation of the correct length of the distal portion of the shunt within the suprarenal IVC.

(7) At this time, inflation of the suprarenal IVC occlusion balloon—now balloon 2—with saline, would achieve the aims of the shunt namely (1) occlusion of the IVC above the renal veins, (2) diversion of blood from the renal veins and the infrarenal IVC through the caudal opening in the device into the shunt and exit of blood through the atrial opening of the shunt to the heart and (3) isolation and bypass of the retrohepatic IVC thereby producing conditions anatomically and physiologically suitable for surgery. This is figuratively represented in FIG. 5.

Technique of Removal

Following repair of the vena cava, and completion of the operation, the balloons can be deflated by the complete withdrawal of saline through the ports -2'- through -5'- and extraction of the shunt through the atriotomy or venotomy, after which the atriotomy or venotomy is closed by a using a standard technique.

Summary

A device has been proposed for achieving the bypass of venous blood away from the retrohepatic IVC and the shunting of blood from the renal veins and the infrarenal IVC through the internal IVC shunt to the heart thereby achieving optimal conditions for surgery in this difficult to access location.

The unique features of the shunt include the following:

1.) Its dimensions are based on the relatively constant known anatomy of the suprarenal IVC and is dedicated to the shunting of blood in this difficult to access retrohepatic segment of the IVC.

2.) It provides a mechanism for the digital sensing of the exact point for fixation of the device at the atriocaval junction within the pericardium which obligates simultaneously (1) the atrial opening of the device to seat within the right atrium, (2) the caudal IVC occlusion balloon to position below the retrohepatic IVC and above the renal vein orifices, (3) The caudal opening of the shunt to admit blood from the renal veins and the infrarenal IVC following the saline inflation of the IVC occlusion balloon around the shunt immediately cephalad to said opening.

This dimensionally correct device and method of fixation eliminates the need for the customization of devices not originally designed for use in the vena cava.

It is anticipated that the proposed device for which a patent is hereby applied will enormously simplify and expedite retrohepatic IVC shunting and can be expected to reduce the horrendous mortality attendant to hemorrhage from injuries in this location, under military and civilian conditions.

Given the benefits to be realized, a speedy and favorable deliberation is implored.

TABLE I

| Measurements by Computerized Tomography | | RA-RRV in m.m. | RA-LRV in m.m. |
|---|---|---|---|
| Adult Men | (27) | 132.2 | 134.2 |
| Adult Women | (23) | 123.2 | 124.2 |

RA = Right Atrium
m.m. = millimeters
RRV = Right Renal Vein
LRV = Left Renal Vein

TABLE II

LEGEND FOR IVC SHUNT (ANDERSON)

FIG. 1 - Shunt (1:I)
FIG. 1C - Cross Section (2:I).
FIG. 2 - Percutaneous Shunt (1:I).
FIG. 2C - Cross Section (2:I)
FIG. 3 - Percutaneous Shunt in caudad insertion.
FIG. 4 - Shunt in IVC.
FIG. 5 - Shunt in IVC m mfra renal access.
1 - Openings in the shunt.
2 - Proximal shunt balloon.
3 and 4 - IVC balloons.
5 - Distal shunt balloon.
6 - Proximal end of shunt with inflation ports 2', 3', 4' and 5' corresponding to balloons 2–5.
7 - Guide wire.
8 - Right Atrium.
9 - IVC.
10 - Renal Vein Office.
11 - Ligature around intrapericardial IVC.
11' - Ligature around right atrial shunt insertion site
12 - tubes in wall of shunt for saline inflation and guide wire
13 - Diaphragm.
14 - Pericardiurm
15 - 1 m.m. circular elevation around shunt.
16 - 2 m.m. central tube in proximal device.
17 - Venous access port.

What is claimed is:

1. A by-pass shunt for insertion into the atrio-venous system to prevent blood from entering the retrohepatic vena cava and to shunt renal and infra renal inferior vena cava blood into the heart, comprising:
   a flexible tube configured to be completely embodied in the atrio-venous system;
   two side-wall orifices in the flexible tube separated mid-orifice to mid-orifice by a distance of about 140 mm; and
   a central duct within the flexible tube connecting the sidewall orifices and having the same diameter as the orifices.

2. A shunt according claim 1, wherein the side-wall orifices and the central duct connecting the side-wall orifices are about 7 to 10 mm in diameter.

3. A shunt according to claim 1, wherein the flexible tube has an external diameter of at least 10 mm but not more than 13 mm, and a length of about 160 mm.

4. A shunt according to claim 1, further comprising:
   a number of inflatable and deflatable balloons encircling the flexible tube and disposed between the side-wall orifices.

5. A shunt according to claim 4, wherein the balloons encircling the flexible tube are inflatable to a diameter of about 35 mm.

6. A shunt according to claim 4, further comprising:
   an elevated ridge encircling the peripheral wall of the flexible tube at the base of each of the inflatable and deflatable balloons closest to the side-wall orifices, to provide for redundant tactile differential sensation.

7. A shunt according to claim 4, wherein the shunt is symmetrical about its mid-transverse axis to confer equal utility in both atrial and infra-renal venous insertion.

8. A shunt according to claim 4, wherein the flexible tube is a first flexible tube, and further comprising:
   a second flexible tube continuous with the first flexible tube, the second flexible tube being configured for manipulation of and introduction of fluids into the first flexible tube.

9. A shunt according to claim 8, further comprising:
   external ports on the second flexible tube for introducing fluids into and removing fluids from the inflatable and deflatable balloons; and
   fluid conduits within the walls of the first and second flexible tubes connecting the inflatable and deflatable balloons to the ports.

10. A shunt according to claim 8, wherein the total length of the first and second flexible tubes is about 50 cm.

11. A by-pass shunt for insertion within the atrio-venous system to divert blood around the retrohepatic vena cava into the heart, comprising:
    a flexible tube configured to be completely embodied in the atrio-venous system, the flexible tube being symmetrical about its mid-transverse and having a length to confer equal utility in both atrial and infra-renal venous insertion;
    two side-wall orifices in the flexible tube; and
    a central duct within the flexible tube connecting the side-wall orifices and having the same diameter as the orifices.

12. A shunt according claim 11, wherein the side-wall orifices and the central duct connecting the side-wall orifices are about 7 to 10 mm in diameter and the mid-orifice to mid-orifice distance between the orifices is about 140 mm.

13. A shunt according to claim 11, wherein the flexible tube has an external diameter of at least 10 mm but not more than 13 mm, and a length of about 160 mm.

14. A shunt according to claim 11, further comprising:
    a number of inflatable and deflatable balloons encircling the flexible tube and disposed between the side-wall orifices.

15. A shunt according to claim 14, wherein the balloons encircling the flexible tube are inflatable to a diameter of about 35 mm.

16. A shunt according to claim 14, further comprising:
    an elevated ridge encircling the peripheral wall of the flexible tube at the base of each of the inflatable and deflatable balloons closest to the side-wall orifices, to provide for redundant tactile differential sensation.

17. A shunt according to claim 14, wherein the flexible tube is a first flexible tube, and further comprising:
    a second flexible tube continuous with the first flexible tube, the second flexible tube being configured for manipulation of and introduction of fluids into the first flexible tube.

18. A shunt according to claim 17, further comprising:
    external ports on the second flexible tube for introducing fluids into and removing fluids from the inflatable and deflatable balloons; and
    fluid conduits within the walls of the first and second flexible tubes connecting the inflatable and deflatable balloons to the ports.

19. A shunt according to claim 17, wherein the total length of the first and second flexible tubes is about 50 cm.

20. A shunt according to claim 17, further comprising:

a guide wire within the wall of the second flexible tube for use in inserting the shunt into the atrio-venous system.

21. A shunt according to claim 17, wherein the second flexible tube includes a separate conduit for introducing fluids into and withdrawing fluids from the central duct of the first flexible tube.

22. A by-pass shunt for insertion into the atrio-venous system, comprising:

a flexible tube having a proximal portion and a distal portion, the proximal portion being configured to manipulate the distal portion, the distal portion being configured to be completely embodied in the atrio-venous system and having two side-wall orifices, the side-wall orifices being connected to each other by a central duct in the distal portion having the same diameter as the orifices and being so spaced, with a predetermined length mid-orifice to mid-orifice, as to be able to shunt renal and infra renal inferior vena cava blood into the right atrium of the heart of an average adult patient;

four inflatable and deflatable balloons encircling the distal portion and disposed between the side-wall orifices;

external ports on the proximal portion for introducing fluids into and removing fluids from the inflatable and deflatable balloons; and fluid conduits within the wall of the flexible tube connecting the inflatable and deflatable balloons to the port means.

* * * * *